(12) United States Patent
Han et al.

(10) Patent No.: US 10,914,727 B2
(45) Date of Patent: Feb. 9, 2021

(54) MICROFLUIDIC PLATFORM DEVICE AND METHOD FOR IDENTIFYING NEUTRALIZING AND/OR ENHANCING ANTIBODIES THROUGH DIRECT FUNCTIONAL ASSAYS

(71) Applicant: The Texas A&M University System, College Station, TX (US)

(72) Inventors: Arum Han, College Station, TX (US); Paul J. de Figueiredo, College Station, TX (US)

(73) Assignee: The Texas A&M University System, College Station, TX (US)

( * ) Notice: Subject to any disclaimer, the term of this patent is extended or adjusted under 35 U.S.C. 154(b) by 178 days.

(21) Appl. No.: 15/750,022

(22) PCT Filed: Aug. 19, 2016

(86) PCT No.: PCT/US2016/047804
§ 371 (c)(1),
(2) Date: Feb. 2, 2018

(87) PCT Pub. No.: WO2017/031438
PCT Pub. Date: Feb. 23, 2017

(65) Prior Publication Data
US 2018/0231522 A1     Aug. 16, 2018

Related U.S. Application Data

(60) Provisional application No. 62/207,261, filed on Aug. 19, 2015.

(51) Int. Cl.
| | | |
|---|---|---|
| *G01N 33/50* | (2006.01) | |
| *B01L 3/02* | (2006.01) | |
| *B01L 3/00* | (2006.01) | |

(52) U.S. Cl.
CPC ........ *G01N 33/5023* (2013.01); *B01L 3/0241* (2013.01); *B01L 3/502784* (2013.01); *G01N 33/5052* (2013.01); *B01L 2200/0652* (2013.01); *B01L 2200/0673* (2013.01); *B01L 2200/10* (2013.01)

(58) Field of Classification Search
None
See application file for complete search history.

(56) References Cited

U.S. PATENT DOCUMENTS

| | | |
|---|---|---|
| 2002/0168671 A1 | 11/2002 | Burns et al. |
| 2009/0005254 A1 | 1/2009 | Griffiths et al. |
| 2009/0068170 A1 | 3/2009 | Weitz et al. |

(Continued)

FOREIGN PATENT DOCUMENTS

WO    WO-2015/112985 A1    7/2015

*Primary Examiner* — Rebecca M Giere
(74) *Attorney, Agent, or Firm* — Winstead PC

(57) ABSTRACT

The microfluidic platform device of the claimed invention makes use of a high throughput lab-on-a-chip format to determine the functional profile of antibodies elicited by infection or vaccination against infection for any pathogen. It can be used to evaluate vaccines, evaluate whether vaccinated individuals show indices of protection, determine whether individuals display resistance or susceptibility to infection, discover new vaccine antigens, discover and test therapeutic interventions, or evaluate mechanisms of disease.

9 Claims, 2 Drawing Sheets

(56) References Cited

U.S. PATENT DOCUMENTS

| | | |
|---|---|---|
| 2009/0203063 A1 | 8/2009 | Wheeler et al. |
| 2011/0166027 A1 | 7/2011 | Weiner |
| 2012/0015347 A1* | 1/2012 | Singhal ............ B01L 3/502761 |
| | | 435/5 |
| 2012/0220497 A1 | 8/2012 | Jacobson et al. |
| 2014/0193807 A1 | 7/2014 | Pamula et al. |
| 2014/0256595 A1 | 9/2014 | Link et al. |
| 2015/0027892 A1 | 1/2015 | Miller et al. |

* cited by examiner

MICROFLUIDIC PLATFORM DEVICE AND METHOD FOR IDENTIFYING NEUTRALIZING AND/OR ENHANCING ANTIBODIES THROUGH DIRECT FUNCTIONAL ASSAYS

CROSS-REFERENCE TO RELATED APPLICATIONS

This application claims priority to and incorporates by reference the entire disclosure of U.S. Provisional Patent Application No. 62/207,261 filed on Aug. 19, 2015.

BACKGROUND OF THE INVENTION

Current vaccine and therapeutic development efforts require lengthy and costly clinical trials, which can take over ten years to complete and can incur hundreds of millions of dollars in costs. Vaccine development is heavily constrained by a lack of fast and reliable approaches for predicting their efficacy. Vaccine development is further daunted by high rates of failure that are typically unrecognizable until hundreds-of-millions of dollars have been invested in time-consuming preclinical and clinical trials. The risk of failure is even greater amongst cases where relevant animal models are not available as the efficacy cannot be reliably predicted until Phase II clinical trials have been completed many years after preclinical testing.

Current approaches for identifying the complete repertoire of antibody (Ab) functions elicited by vaccination or natural infection are costly, time consuming, and often unsuccessful because of multiple intrinsic assay limitations that introduce significant outcome bias prior to any assessment of neutralizing function. Conventional bioassays for measuring neutralizing antibody (nAb) or enhancing antibody (eAb) activities rely on findings from experiments with polyclonal sera. The activity of polyclonal sera represents the summation of a plurality of antibodies and does not allow for a precise accounting of clonal nAb or eAb activities to be measured. Current approaches are further limited by the use of conventional limiting dilution to isolate and characterize Abs produced by individual B cells, which has limited throughput, greatly constraining the evaluation of the Ab repertoire. Current approaches also rely heavily on methods possessing significant intrinsic bias at multiple stages along the Ab generation. Abundant Ab-producing B-cells generated in vivo will override the selection of rare, antigen-specific Ab-producing B-cells in vitro when approaches rely on "population-based" assays instead of "single cell based" assays. Substantial bias may also be introduced by the fact that polyclonal populations of primary antigen-specific B-cells often require fusion with an immortalized cell line (hybridoma creation) to make culture more facile. The claimed invention attempts to ameliorate these limitations and biases.

SUMMARY OF THE INVENTION

The microfluidic platform device of the claimed invention makes use of a high throughput lab-on-a-chip format named PRESCIENT (Platform for the Rapid Evaluation of SucCessful antibody activities using Integrated microfluidics Enabled Technology) to determine the functional profile of antibodies elicited by infection or vaccination against infection for any pathogen. It can thus be used to evaluate vaccines, evaluate whether vaccinated individuals show indices of protection, determine whether individuals display resistance or susceptibility to infection, discover new vaccine antigens, discover and test therapeutic interventions, or evaluate mechanisms of disease.

Antibody producing cells are first cultivated in droplets, quantitatively evaluated on their production of neutralizing antibodies and enhancing antibodies through a direct functional assay, and sorted based upon the detection of a neutralized and uninfected "hit" or a highly infectious and enhancing "hit."

DETAILED DESCRIPTION

Embodiments of the claimed invention are directed to a microfluidic platform device 100 and method for identifying neutralizing and/or enhancing antibodies through direct functional assays named PRESCIENT (Platform for the Rapid Evaluation of SucCessful antibody activities using Integrated microfluidics Enabled Technology) or COMMANDO (Comprehensive Microfluidic Microsystem for Identifying Antibodies that Neutralize biodefense-related Organisms) that will enable the comprehensive determination of the functional repertoire of Abs elicited by vaccines or patients.

PRESCIENT performs three distinct tasks at single-cell resolution in a high throughput lab-on-a-chip format. PRESCIENT will first cultivate B cells (e.g., memory B cells, or B(mem)s) derived from vaccinated or infected animals or convalescent patients. PRESCIENT will then perform quantitative evaluation of nAbs and/or eAbs produced by pathogen-specific B cells through direct functional assays. PRESCIENT will lastly sort the B cells that synthesize nAbs and/or eAbs.

Figure 1:
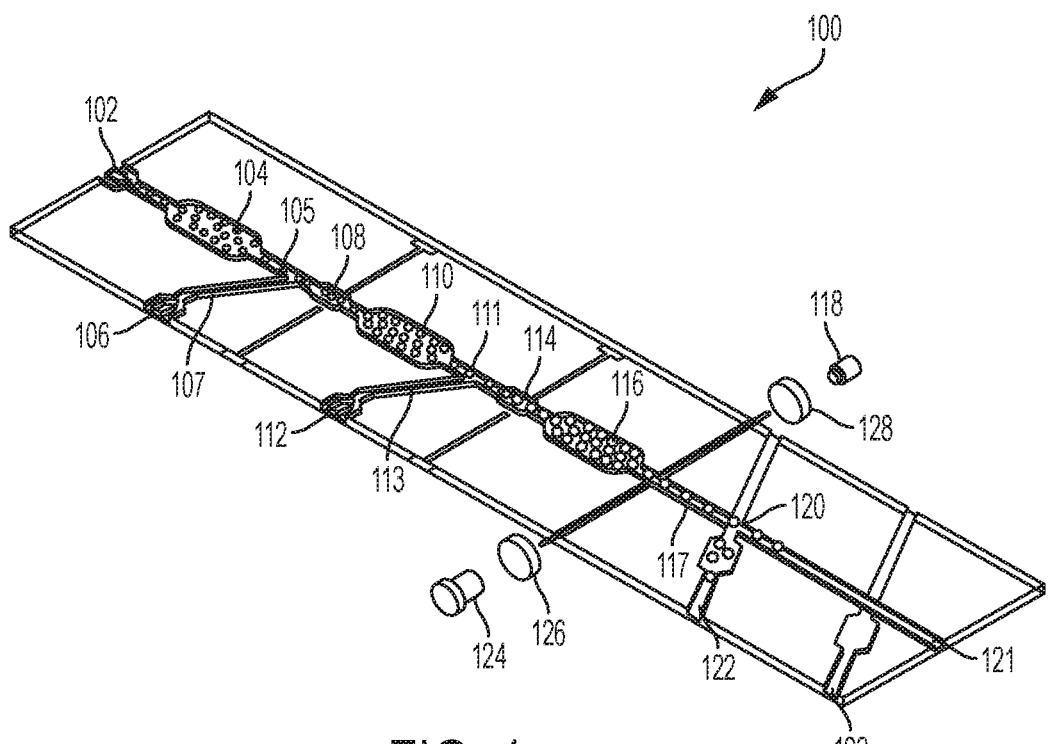
FIG. 1 illustrates a microfluidic platform device.
Figure 2:
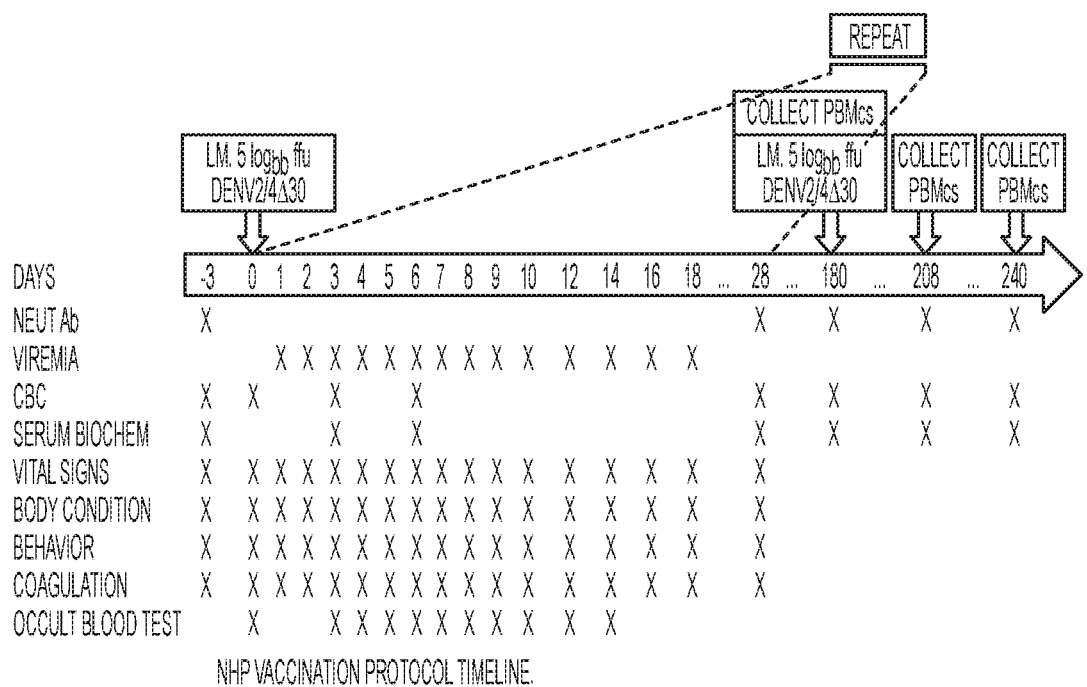
FIG. 2 illustrates a typical non-human primate (NHP) vaccination immunization protocol timeline.

Referring now to FIG. 1, a microfluidic platform device 100 for identifying, neutralizing, and/or enhancing antibodies is shown. The microfluidic platform device 100 uses functional assays to detect where B cells are first cultivated in order to perform a quantitative evaluation of nAbs and/or eAbs produced by pathogen-specific B cells so that these cells may be sorted by their capability to synthesize eAbs and/or nAbs. As shown in FIG. 1, the microfluidic platform device 100 includes a first droplet generator 102 that encapsulates single Ab-producing cells into microdroplets, a first droplet incubation chamber 104 for Ab accumulation, a second droplet generator 106 that encapsulates infectious agents, a droplet merging region 108 to merge these two droplets (e.g. electric field based, surface tension based droplet merging), a second droplet incubation chamber 110 to co-incubate the Ab-producing B cells and pathogens, reporter viral particles (RVP), or other agents to allow neutralization (or enhancement) of the agents to take place, a third droplet generator 112 encapsulating host cells that may be engineered to express a fluorescent reporter upon infection with pathogens, a second droplet merging region 114 that merges the two droplets, a third droplet incubation chamber 116 that allows the neutralization (or enhancement) assay to take place, and a droplet fluorescence detector 118 that identifies droplets that contain uninfected reporter host cells with a droplet sorter 120 to sort between neutralized and uninfected "hits" that exit an outlet 122 or enhanced and highly infected "hits" that exit an outlet 123 so that they may be later sent off chip to allow for B cell recovery and further analysis. Droplets with no effect will continue to flow out of outlet 121.

In a typical embodiment, an assay for using the microfluidic platform device 100 begins by adding assay components to the microfluidic platform device 100. The assay components may include a B cell encapsulation that is introduced to the microfluidic platform device 100 via the first droplet generator 102. The B cell encapsulation proceeds to the first droplet incubation chamber 104 for Ab accumulation. An RVP encapsulation is introduced to the microfluidic platform device 100 via the second droplet generator 106 that feeds the RVP encapsulation to a merger conduit 105 via a conduit 107. The RVP encapsulation and the B cell encapsulation are merged in the droplet merging region 108. The merged droplets are fed into the second droplet incubation chamber 110, where the assay is performed.

Within the second droplet incubation chamber 110, Ab binds to the RVP encapsulation. Host cells encapsulated into a droplet through the third droplet generator 112 are introduced to the microfluidic platform device 100 via a conduit 113 that feeds into a merger conduit 111 and droplet merging region 114. The merged droplet containing the Ab/RVP encapsulation and the host cells are then moved to the third droplet incubation chamber 116. Neutralization and antibody-dependent enhancement assay (ADE) occurs within the third droplet incubation chamber 116. Upon exiting the third droplet incubation chamber 116, light from a light source 124 is directed towards a conduit 117 where the merged droplet within which the assay (e.g., neutralization, enhancement, or no effect) occurs is passing through. Light that passes through the assayed Ab composition is analyzed by the droplet fluorescence detector 118. In a typical embodiment, the light from the light source 124 is filtered via an excitation filter 126 (if using a broad band light source) prior to passing through the assayed Ab composition and is filtered again after passing through the assayed Ab composition by an emission filter 128 prior to reaching the droplet fluorescence detector 118. In a typical embodiment, the detector 118 comprises a photomultiplier tube (PMT) or photodiode (PD). The droplet fluorescence detector 118 analyzes the fluorescence of the assayed Ab composition. If using a host cell and/or RVP engineered to express fluorescence upon infection of the host cell, droplets that contain B cells that produces Ab with no specificity will result in moderate level of fluorescence, indicating that the host cells have been infected. If a droplet contains B cells that produce nAbs, this will result in either reduced level of infection or no infection, resulting in reduced fluorescence intensity or no fluorescence. If a droplet contains B cells that produce eAbs, this will result in higher fluorescence signal. Thus the level of fluorescence will be used as a criteria to sort droplets that contain potential "hits" of neutralization or enhancement.

After passing through the light from the light source 124, the droplet containing assayed Ab composition passes through a conduit 117 to the droplet sorter 120. The droplet sorter 120 sorts between neutralized and uninfected "hits" that exit the outlet 122 and enhanced and highly infected "hits" that exit the outlet 123 so that they may be later sent off chip to allow for B cell recovery and further analysis.

In an embodiment of the invention, the microfluidic platform device 100 will be made from polydimethyl siloxane (PDMS) using standard soft lithography techniques. In certain embodiments where a large amount of devices is required, the microfluidic platform device will instead be made in plastic by using injection molding or other methods.

The microfluidic platform device 100 may be utilized to determine the functional profile of Abs elicited by infection or vaccination against infection for any pathogen. In certain embodiments, the microfluidic platform can be used to develop new vaccines and discover new vaccine antigens. In other embodiments, the microfluidic platform 100 may be utilized to provide a vaccine or therapeutics evaluation service. Compared to conventional vaccine development pipelines, the microfluidic platform device 100 offers numerous advantages. For example, in the vaccine antigen discovery phase, the microfluidic platform device 100 enables rapid, unbiased and relative low cost identification of preclinical vaccine candidates, which further enables identification of ideal vaccine antigens and epitopes. In the preclinical evaluation phase, the microfluidic platform device 100 also enables a determination of strongly and weakly neutralizing activities elicited and a determination of potentially enhancing antibodies elicited. In the clinical trial phase, the microfluidic platform device 100 enables accelerated and comprehensive analysis of vaccine trial findings and analysis of the antibody functions elicited in vaccinated patients. Table 1 below illustrates additional advantages of the PRESCIENT-enabled approach made possible by the microfluidic platform device 100 as compared to conventional techniques. The single-cell resolution assay and the use of B cells without creating hybridoma cells allow unbiased screening that enable the identification of near-complete Ab repertoire. The discovery of large number of B cells that potentially produces nAbs and/or eAbs will contribute to global understanding of the entire Ab repertoire rather than just a sub-set when using conventional assays (due to time and effort needed in such assays). Droplet microfluidics of the PRESCIENT where all functional steps can be conducted typically in tens to thousands of assays per second enable high-throughput screening with much higher speed compared to conventional assays.

TABLE 1

Conventional vs. PRESCIENT-enabled approach
PRESCIENT Advantages

| Conventional | PRESCIENT |
| --- | --- |
| Biased | Unbiased |
| Indirect analysis | Direct functional analysis |
| Low throughput ($10^2$) assays/day | High throughput ($10^7$ assays/day) |
| Incomplete analysis | Near-complete analysis |
| Months to perform | Days to perform |
| Multicellular resolution | Single cell resolution |
| Small subset of hits | Global understanding |

In an embodiment of the invention, the microfluidic platform device 100 may be utilized to create new antibody-based therapeutics.

In an embodiment of the invention, the microfluidic platform device 100 will perform high throughput screens that feature direct functional assays for B cells (e.g., B(mem)s) in order to determine if the antibodies produced either neutralize or enhance host cell infection by virus or viral particles.

In an embodiment of the invention, the microfluidic platform device 100 may be used with any source of antibody producing cells, such as, for example, primary B cells, immortalized B cells, hybridoma cells, mammalian cells that produce and/or secrete antibodies, yeast or other eukaryotic cells that produce and/or secrete antibodies, and bacterial cells that produce and/or secrete antibodies. In certain embodiments, the microfluidic platform device 100 may also be used in conjunction with cells that produce and/or secrete non-antibody based capture reagents (including but not limited to) aptamers comprised of DNA, RNA, or synthetic nucleic acids and capture reagents comprised of natural or synthetic proteins.

In an embodiment of the invention, the microfluidic platform device parameters may be optimized in various ways such as (but not limited to) hybridoma cell or primary B cell survival and replication rate, Ab production rate over time, efficiency of RVP entry into host cells and reporter expression levels, times of co-incubation of nAb and RVPs required for neutralization, duration of RVP co-incubation with host cells, levels of neutralizing activities against RVPs of the Abs produced in droplets, and sorting and off-chip recovery of droplets containing hybridoma cells that produce nAbs (or eAbs).

Conditional language used herein such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. While the above detailed description has shown, described, and pointed out novel features as applied to various embodiments, it will be understood that various omissions, substitutions, and changes in the form and details of the devices illustrated can be made without departing from the spirit of the disclosure. As will be recognized, the processes described herein can be embodied within a form that does not provide all of the features and benefits set forth herein, as some features can be used or practiced separately from others. The scope of protection is defined by the appended claims rather than by the foregoing description. All changes which come within the meaning and range of equivalency of the claims are to be embraced within their scope.

What is claimed is:

1. A method of identifying, neutralizing, and enhancing antibody repertoire comprising:
   encapsulating one or more antibody producing cells into a first droplet;
   accumulating antibodies;
   encapsulating infectious agents within a second droplet;
   merging the antibody producing droplet with the infectious agent droplet;
   co-incubating the antibody producing B cells and the infectious agents to allow neutralization or enhancement of the infections agents to take place to form a combination droplet;
   encapsulating reporter host cells within a third droplet;
   merging the combination droplet with the reporter host cell droplet;
   allowing a neutralization or enhancement assay to take place;
   identifying droplets that contain uninfected reporter host cells or highly infected reporter host cells;
   sorting the droplets into a first group comprising the droplets that contain uninfected reporter host cells and second group comprising the droplets that contain highly infected reporter host cells; and
   recovering the sorted droplets.

2. The method of claim 1 wherein the encapsulating of the one or more antibody producing cells into a first droplet is performed by a first droplet generator.

3. The method of claim 1 wherein the accumulating antibodies occurs in a first droplet incubation chamber.

4. The method of claim 1 wherein the encapsulating infectious agents is performed by a second droplet generator.

5. The method of claim 1 wherein the merging of the antibody producing droplet with the infectious agent droplet occurs in a first droplet merging region.

6. The method of claim 1 wherein the co-incubating the Ab-producing B cells and the infectious agents occurs within a second droplet incubation chamber.

7. The method of claim 1 wherein the encapsulating the reporter host cells is performed by a third droplet generator.

8. The method of claim 1 wherein the merging the combination droplet with the reporter host cell droplet occurs within a second droplet merging region.

9. The method of claim 1 wherein the neutralization or enhancement assay occurs within a third droplet incubation chamber.

\* \* \* \* \*